(12) United States Patent
Liu et al.

(10) Patent No.: US 8,227,493 B2
(45) Date of Patent: Jul. 24, 2012

(54) DISPERSIBLE PESTICIDAL COMPOSITIONS

(75) Inventors: Hong Liu, Pennington, NJ (US); Robin Dexter, Yardley, PA (US); Timothy Martin, Ringoes, NJ (US); Craig Martin, Morrisville, PA (US)

(73) Assignee: FMC Corporation, Philadelphia, PA (US)

( * ) Notice: Subject to any disclaimer, the term of this patent is extended or adjusted under 35 U.S.C. 154(b) by 762 days.

(21) Appl. No.: 11/578,005

(22) PCT Filed: Apr. 13, 2005

(86) PCT No.: PCT/US2005/012398
§ 371 (c)(1),
(2), (4) Date: Jul. 24, 2007

(87) PCT Pub. No.: WO2005/104846
PCT Pub. Date: Nov. 10, 2005

(65) Prior Publication Data
US 2010/0120870 A1    May 13, 2010

Related U.S. Application Data

(60) Provisional application No. 60/562,071, filed on Apr. 14, 2004.

(51) Int. Cl.
*A01N 43/40* (2006.01)
*A61K 31/41* (2006.01)

(52) U.S. Cl. ........ 514/355
(58) Field of Classification Search ........ None
See application file for complete search history.

(56) References Cited

U.S. PATENT DOCUMENTS

| | | | | |
|---|---|---|---|---|
| 3,986,979 A | * | 10/1976 | Moorer et al. | 516/77 |
| 4,731,379 A | * | 3/1988 | Panzer | 514/547 |
| 4,936,901 A | * | 6/1990 | Surgant et al. | 504/133 |
| 5,360,806 A | * | 11/1994 | Toki et al. | 514/318 |
| 5,462,915 A | * | 10/1995 | Curtis et al. | 504/323 |
| 6,291,412 B1 | | 9/2001 | Kvita et al. | |
| 6,387,388 B1 | | 5/2002 | Misselbrook | |
| 2002/0114821 A1 | | 8/2002 | Lescota | |
| 2003/0036544 A1 | * | 2/2003 | Steiger et al. | 514/242 |

FOREIGN PATENT DOCUMENTS

| | | |
|---|---|---|
| EP | 0 749 688 A2 | 12/1996 |
| WO | WO 97/16968 A1 | 5/1997 |
| WO | WO 0001234 A1 * | 1/2000 |

OTHER PUBLICATIONS http://www.belchim.com/pdf/UK/Teppeki-20(E)-202003-11-01-20V2.pdf, accessed on Aug. 30, 2010.*

* cited by examiner

*Primary Examiner* — Brandon Fetterolf
*Assistant Examiner* — Jean Cornet
(74) *Attorney, Agent, or Firm* — FMC Corporation

(57) ABSTRACT

Soluble granule pesticidal compositions comprise Flonicamid, a dispersant, and a wetting agent are disclosed.

7 Claims, No Drawings

DISPERSIBLE PESTICIDAL COMPOSITIONS

This application claims the benefit of U.S. Provisional Application No. 60/562,071, filed Apr. 14, 2004.

FIELD OF THE INVENTION

The present invention relates to pesticidal compositions. In particular, the invention provides a soluble granule formulation of Flonicamid, a water-soluble pesticide, which is easily dispersed in an aqueous medium.

BACKGROUND OF THE INVENTION

To enable the efficient elimination or controlling of unwanted pests, it is desirable to use effective chemical pesticides on these unwanted pests. Soluble granule formulations containing water-soluble pesticides are desirable in agricultural and related endeavors due to ease of handling and the elimination of organic solvents, which can be costly and dangerous to the environment. Safety, specifically eye irritation, caused by solvents, dispersants, clays and wetting agents in traditional formulations are also of concern. In addition, the process used to make the soluble granule formulation can be conducted in relatively simple equipment using relatively simple process steps.

The formulation of soluble granule pesticides has been disclosed in the prior art, for example in U.S. Pat. No. 6,387,388 (Misselbrook et al.). Challenges in formulating a soluble granule of a water-soluble pesticide include the requirements that the final product successfully achieves (a) good dispersibility/solubility in an aqueous medium and (b) chemical stability once dispersed.

Good dispersibility/solubility in an aqueous medium is important in a soluble granule formulation since ineffective mixing of the pesticide into solution can result in reduced or inconsistent efficacy and, ultimately, costly returns of product and loss of sales. Chemical degradation is also important because there may be no physical sign of the degradation and resultant loss of efficacy until used on a pest. Examples of problematic chemical degradation include hydrolysis, oxidation, dehalogenation and bond cleavage.

SUMMARY OF THE INVENTION

The present invention is directed to a soluble granule composition comprising Flonicamid, a dispersant, and a wetting agent. This soluble granule composition has improved dispersibility/solubility as compared to other formulations.

DETAILED DESCRIPTION OF THE INVENTION

As used in this specification and unless otherwise indicated the term "Flonicamid" refers to N-cyanomethyl-4-trifluoromethyl nicotinamide, or salts thereof. The term "pesticide" refers to a molecule or combination of molecules that repels, retards, or kills pests, such as, but not limited to, deleterious or annoying insects, weeds, worms, fungi, bacteria, and the like, and can be used for crop protection, edifice protection, turf protection, or protection of a person; pesticide as used herein includes, but is not limited to, herbicides, insecticides, acaricides, fungicides, nematicides, ectoparasiticides, and growth regulators, either used to encourage growth of a desired plant species or retard growth of an undesired pest.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated the substituent terms "alkyl", "cycloalkyl", "alkoxy", "aryloxy", and "alkoxyarylamino", used alone or as part of a larger moiety, includes straight or branched chains of at least one or two carbon atoms, as appropriate to the substituent, and preferably up to 20 carbon atoms, more preferably up to ten carbon atoms, most preferably up to seven carbon atoms. "Halogen" or "halo" refers to fluorine, bromine, iodine, or chlorine. "Aryl" refers to an aromatic ring structure having 5 to 10 carbon atoms.

The term "ambient temperature" as utilized herein shall mean any suitable temperature found in a laboratory or other working environment, and is generally not below about 15° C. nor above about 30° C.

The present invention is directed to a soluble granule composition comprising Flonicamid, a dispersant, and a wetting agent. The invention can further comprise a water-soluble carrier.

Flonicamid can be present in a concentration of from 1% by weight to 94% by weight, more particularly 45% by weight to 55% by weight, based upon the total weight of all components in the composition.

The dispersant can be selected from the group consisting of sodium alkyl naphthalene sulfonate formaldehyde condensate, modified acrylate copolymer (sodium salt), alkyl naphthalene sulfonate salts and dodecyl benzene sulfonate (Na) salt. Preferably, the dispersant is sodium alkyl naphthalene sulfonate formaldehyde condensate. The dispersant can be present in a concentration of from 0.5% by weight to 20% by weight, more particularly 2% by weight to 6% by weight, based upon the total weight of all components in the composition.

The wetting agent can be selected from the group consisting of a mixture of sodium dioctylsufosuccinate and sodium benzoate wherein the sodium dioctylsufosuccinate is up to 85 weight percent, polyalkylencoxide modified heptamethyl trisiloxane, alkyloxypolyethylene glycol methyl ether and alcohol (C8-C16) ethoxylates with 3-20 moles of ethylene oxide. Preferably, the wetting agent is a mixture of sodium dioctylsufosuccinate and sodium benzoate wherein the sodium dioctylsufosuccinate is present in a concentration up to 85 weight percent. The wetting agent can be present in a concentration of from 0.1% by weight to 20% by weight, more particularly 0.5% by weight to 3% by weight, based upon the total weight of all components in the composition.

The water-soluble carrier can be selected from the group consisting of lactose, sucrose, glucose, starch, sodium tripolyphosphate and water-soluble salts. Preferably, the water-soluble carrier is lactose. The water-soluble carrier can be present in a concentration of from 0.001% by weight to 97% by weight, more particularly 35% by weight to 45% by weight, based upon the total weight of all components in the composition.

Another embodiment of the present invention is a soluble granule composition comprising Flonicamid; a dispersant selected from the group consisting of sodium alkyl naphthalene sulfonate formaldehyde condensate, modified acrylate copolymer (sodium salt), alkyl naphthalene sulfonate salts and dodecyl benzene sulfonate (Na) salt; a wetting agent selected from the group consisting of a mixture of sodium dioctylsufosuccinate and sodium benzoate wherein the sodium dioctylsufosuccinate is present in a concentration up to 85 weight percent, polyalkylencoxide modified heptamethyl trisiloxane, alkyloxypolyethylene glycol methyl ether and alcohol (C8-C16) ethoxylates with 3-20 moles of ethylene oxide; and a water-soluble carrier selected from the group consisting of lactose, sucrose, glucose, starch, sodium tripolyphosphate and water-soluble salts.

Another embodiment of the present invention is a soluble granule composition comprising from 1% to 94% of Flonicamid, from 0.5% to 20% of sodium alkyl naphthalene sulfonate formaldehyde condensate, from 0.1% to 20% of a mixture of sodium dioctylsufosuccinate and sodium benzoate wherein the sodium dioctylsufosuccinate is present in a concentration up to 85%, and from 0.001% to 97% of lactose, wherein all % are % by weight based upon the total weight of all components in the composition.

Yet another embodiment of the present invention is a soluble granule composition comprising from 25% to 88% of Flonicamid, from 0.5% to 20% of sodium alkyl naphthalene sulfonate formaldehyde condensate, from 0.4% to 5.0% of a mixture of sodium dioctylsufosuccinate and sodium benzoate wherein the sodium dioctylsufosuccinate is present in a concentration up to 85%, and from 6% to 70% of lactose, wherein all % are % by weight based upon the total weight of all components in the composition.

Yet another embodiment of the present invention is a soluble granule composition comprising from 45% to 55% of Flonicamid, from 2% to 6% of sodium alkyl naphthalene sulfonate formaldehyde condensate, from 0.5% to 3% of a mixture of sodium dioctylsufosuccinate and sodium benzoate wherein the sodium dioctylsufosuccinate is present in a concentration up to 85%, and from 35% to 45% of lactose, wherein all % are % by weight based upon the total weight of all components in the composition.

The composition may further comprise an anti-foam agent and/or an anti-bacteria agent.

The present invention also encompasses a method of controlling unwanted pests, comprising applying to an area infested with such pests an effective amount of the soluble granule composition, discussed above, in an aqueous solvent.

The present invention also encompasses a process for preparing the soluble granule composition comprising a) forming a mixture of Flonicamid, a dispersant, a wetting agent and, optionally, a water-soluble carrier; b) kneading the mixture; c) extruding the kneaded mixture from step b); and d) drying the extruded mixture from step c). Preferably, the process further comprises milling the mixture prior to kneading.

The pesticidal compositions of the present invention are further illustrated by the examples below. Flonicamid used in all examples contains 97% active ingredient. The examples serve only to illustrate the invention and should not be interpreted as limiting since further modifications of the disclosed invention will be apparent to those skilled in the art. All such modifications are deemed to be within the scope of the invention as defined in the claims.

In the examples below, testing to demonstrate the dispersibility/solubility of the composition was carried out in the following manner: 1) At ambient temperature, 1.0 gram of the composition prepared in the example was added to 100 ml of water in a cylinder of appropriate size; 2) the cylinder was repeatedly inverted 180 degrees to effect dispersion/solution of the composition into the water; 3) the number of inversions required for full dispersion/solution to a clear state was determined visually and recorded. The results of these tests are presented in each example.

EXAMPLE 1

This example illustrates the preparation of a 50SG composition (Composition A) of the present invention.

A mixture of 52.0 grams of Flonicamid, 5.0 grams of sodium alkylnaphthalene sulfonate formaldehyde condensate, 1.0 gram of a combination of sodium dioctylsufosuccinate and sodium benzoate (Aerosol OTB available from Cytec Industries, Inc. in West Paterson, N.J.) and 42.0 grams of lactose were combined and agitated under high shear. To this mixture was added 14.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition A required 3 inversions for full dispersion into a clear solution.

EXAMPLE 2

This example illustrates the preparation of a 50SG composition (Composition B) of the present invention.

A mixture of 52.0 grams of Flonicamid, 5.0 grams of sodium alkylnaphthalene sulfonate formaldehyde condensate, 1.0 gram of a combination of sodium dioctylsufosuccinate and sodium benzoate (Aerosol OTB available from Cytec Industries, Inc. in West Paterson, N.J.) and 42.0 grams of ammonium sulfate were combined and agitated under high shear. To this mixture was added 14.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition B required 8 inversions for full dispersion into a clear solution.

EXAMPLE 3

This example illustrates the preparation of a 50SG composition (Composition C) of the present invention.

A mixture of 52.0 grams of Flonicamid, 4.0 grams of modified acrylate copolymer (sodium salt), 1.0 gram of a combination of sodium dioctylsufosuccinate and sodium benzoate (Aerosol OTB available from Cytec Industries, Inc. in West Paterson, N.J.) and 43.0 grams of sodium tripolyphosphate were combined and agitated under high shear. To this mixture was added 14.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition C required 7 inversions for full dispersion into a clear solution.

EXAMPLE 4

This example illustrates the preparation of a 24SG composition (Composition D) of the present invention.

A mixture of 25.0 grams of Flonicamid, 5.0 grams of sodium alkylnaphthalene sulfonate formaldehyde condensate, 0.5 gram of a combination of sodium dioctylsufosuccinate and sodium benzoate (Aerosol OTB available from Cytec Industries, Inc. in West Paterson, N.J.), 68.45 grams of lactose, 1.0 gram of an anti-bacteria agent (Dowcide A available from Dow Chemical Company in Midland, Mich.) and 0.05 gram of an anti-foam agent were combined and agitated under high shear. To this mixture was added 13.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition D required 5 inversions for full dispersion into a clear solution.

EXAMPLE 5

This example illustrates the preparation of a 24SG composition (Composition E) of the present invention.

A mixture of 25.0 grams of Flonicamid, 5.0 grams of sodium alkylnaphthalene sulfonate formaldehyde condensate, 0.5 gram of a combination of sodium dioctylsufosuccinate and sodium benzoate (Aerosol OTB available from Cytec Industries, Inc. in West Paterson, N.J.) and 69.5 grams of lactose were combined and agitated under high shear. To this mixture was added 13.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition E required 3 inversions for full dispersion into a clear solution.

EXAMPLE 6

This example illustrates the preparation of an 85SG composition (Composition F) of the present invention.

A mixture of 87.6 grams of Flonicamid, 5.0 grams of sodium alkylnaphthalene sulfonate formaldehyde condensate, 1.0 gram of a combination of sodium dioctylsufosuccinate and sodium benzoate (Aerosol OTB available from Cytec Industries, Inc. in West Paterson, N.J.) and 6.4 grams of lactose were combined and agitated under high shear. To this mixture was added 15.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition F required 3 inversions for full dispersion into a clear solution.

EXAMPLE 7

This example illustrates the preparation of a 50SG composition (Composition G) of the present invention.

A mixture of 52.0 grams of Flonicamid, 3.0 grams of sodium alkylnaphthalene sulfonate formaldehyde condensate, 1.0 gram of a combination of sodium dioctylsufosuccinate and sodium benzoate (Aerosol OTB available from Cytec Industries, Inc. in West Paterson, N.J.), 41.5 grams of lactose and 2.5 grams of a mixture of polyalkyleneoxide modified heptamethyl trisiloxane and alkyloxypolyethylene glycol methyl ether (Silwet L-77 available from OSi Specialties, a Crompton Business in Greenwich, Conn.) were combined and agitated under high shear. To this mixture was added 14.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition G (after being stored at −10 C) required 2 inversions for full dispersion into a clear solution.

EXAMPLE 8

This example illustrates the preparation of a 70SG composition (Composition H) of the present invention.

A mixture of 72.0 grams of Flonicamid, 5.0 grams of sodium alkylnaphthalene sulfonate formaldehyde condensate, 1.0 gram of a combination of sodium dioctylsufosuccinate and sodium benzoate (Aerosol OTB available from Cytec Industries, Inc. in West Paterson, N.J.) and 22.0 grams of lactose were combined and agitated under high shear. To this mixture was added 15.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 10 to 15 minutes until the moisture content of the product was less than 1%.

Composition H required 3 inversions for full dispersion into a clear solution.

EXAMPLE 9

This example illustrates the preparation of a 91SG composition (Composition I) of the present invention.

A mixture of 94.0 grams of Flonicamid, 5.0 grams of sodium alkylnaphthalene sulfonate formaldehyde condensate and 1.0 gram of a combination of sodium dioctylsufosuccinate and sodium benzoate (Aerosol OTB available from Cytec Industries, Inc. in West Paterson, N.J.) were combined and agitated under high shear. To this mixture was added 30.0 grams of water and then the mixture was kneaded in a Hobart mixer for about 2 minutes. The kneaded mixture was then extruded in a Fuji Paudal DGL-1 using a dome with 0.8-millimeter apertures. The resultant product was then dried at 60° C. with 80% airflow for 5 to 10 minutes until the moisture content of the product was less than 1%.

Composition I required 3 inversions for full dispersion into a clear solution.

While this invention has been described with an emphasis upon preferred embodiments, it will be obvious to those of ordinary skill in the art that variations in the preferred compositions and methods may be used and that it is intended that the invention may be practiced otherwise than as specifically described herein.

Accordingly, this invention includes all modifications encompassed within the spirit and scope of the invention as defined by the claims that follow.

What is claimed is:

1. A soluble granule composition comprising:
   a) from 45% by weight to 55% by weight based upon the total weight of all components in the composition of Flonicamid;

b) from 2% by weight to 6% by weight based upon the total weight of all components in the composition of a dispersant selected from the group consisting of sodium alkyl naphthalene sulfonate formaldehyde condensate, alkyl naphthalene sulfonate salts and dodecyl benzene sulfonate (Na) salt;

c) from 0.5% by weight to 3% by weight based upon the total weight of all components in the composition of a wetting agent selected from the group consisting of a mixture of sodium dioctylsulfosuccinate and sodium benzoate wherein the sodium dioctylsufosuccinate is present in a concentration up to 85 weight percent; and d) from 35% by weight to 45% by weight based upon the total weight of all components in the composition of a water-soluble carrier selected from the group consisting of lactose, sucrose, glucose, starch, sodium tripolyphosphate and water-soluble salts.

2. The composition of claim 1, wherein the dispersant is sodium alkyl naphthalene sulfonate formaldehyde condensate.

3. The composition of claim 1, wherein the wetting agent is a mixture of sodium dioctylsulfosuccinate and sodium benzoate wherein the sodium dioctylsulfosuccinate is present in a concentration up to 85 weight percent.

4. The composition of claim 1, wherein the water-soluble carrier is lactose.

5. The composition of claim 1, further comprising an anti-foam agent.

6. The composition of claim 1, further comprising an anti-bacteria agent.

7. A soluble granule composition comprising:
   a) from 45% to 55% of Flonicamid;
   b) from 2% to 6% of sodium alkyl naphthalene sulfonate formaldehyde condensate;
   c) from 0.5% to 3% of a mixture of sodium dioctylsulfosuccinate and sodium benzoate wherein the sodium dioctylsulfosuccinate is present in a concentration up to 85%; and
   d) from 35% to 45% of lactose;
   wherein all % are % by weight based upon the total weight of all components in the composition

* * * * *